(12) United States Patent
Burgoyne

(10) Patent No.: US 6,869,769 B2
(45) Date of Patent: Mar. 22, 2005

(54) METHODS AND MATERIALS FOR DETECTING GENETIC MATERIAL

(75) Inventor: Leigh Alexander Burgoyne, Mitchum (AU)

(73) Assignee: Whatman, Inc., Newton, MA (US)

( * ) Notice: Subject to any disclaimer, the term of this patent is extended or adjusted under 35 U.S.C. 154(b) by 0 days.

(21) Appl. No.: 10/298,255

(22) Filed: Nov. 15, 2002

(65) Prior Publication Data

US 2003/0134312 A1 Jul. 17, 2003

Related U.S. Application Data

(60) Provisional application No. 60/336,005, filed on Nov. 15, 2001.

(51) Int. Cl.[7] .............................. C12Q 1/68; C07H 21/04
(52) U.S. Cl. .......................... 435/6; 435/91.1; 435/91.2; 536/23.1; 536/24.3; 536/24.32; 536/24.33
(58) Field of Search .......................... 435/6, 91.1, 91.2; 536/23.1, 24.3, 24.32, 24.33

(56) References Cited

U.S. PATENT DOCUMENTS

| | | | |
|---|---|---|---|
| 5,496,562 A | 3/1996 | Burgoyne | 422/488 |
| 5,756,126 A | 5/1998 | Burgoyne | 424/488 |
| 5,807,527 A | 9/1998 | Burgoyne | 422/488 |
| 5,861,245 A | 1/1999 | McClelland et al. | 435/6 |
| 5,972,386 A | 10/1999 | Burgoyne | 424/488 |
| 5,976,572 A | 11/1999 | Burgoyne | 424/488 |
| 6,294,203 B1 | 9/2001 | Burgoyne | 424/488 |
| 2001/0007746 A1 * | 7/2001 | Smith et al. | 435/6 |
| 2002/0150907 A1 * | 10/2002 | Fomovskaia et al. | 435/6 |

FOREIGN PATENT DOCUMENTS

| | | | |
|---|---|---|---|
| WO | WO 03/016546 A1 | 2/2003 | C12P/19/34 |

OTHER PUBLICATIONS

Craig D.G. Rogers and Leigh A. Burgoyne, "Reverse transcription of an RNA genome from databasing", Biotechnol. Appl. Biochem., 31:219–224 (2000).

Craig Rogers and Leigh A. Burgoyne, "Bacterial Typing: Storing and Processing of Stabilized Reference Bacteria for Polymerase Chain Reaction without Preparing DNA—An Example of an Automatable Procedure", Analytical Biochemistry, 247:223–227 (1997).

James A. Higgins et al., "Detection of *Francisella Tularensis* in Infected Mammals and Vectors Using a Probe–Based Polymerase Chain Reaction", Am. J. Trop. Med. Hyg. 62(2) :310–318 (2000).

C. Rogers, "Amplificaiton of Trace Nucleic Acids" Flinders Technologies Pty. Website, pp. 1–6 (2002), http:// flinderstech.flinders.edu.au/amplification%20trace%20nucleic%20text.htm.

C. Rogers, "ANTA Results", Flinders Technologies Pty. Website, pp. 1–6 (2002), http:// flinderstech.flinders.edu.au/amplification%20trace%20nucleic.diagramhtm.htm.

Neil A.Campbell, Biology Third Edition, Chapter 7: A Tour of the Cell, pp. 121–123, Chapter 17: Microbial Models: The Genetics of Viruses and Bacteria, pp. 345–346.

Geoffrey M. Cooper, The Cell A Molecular Approach, Chapter 1, p. 4, 8–12.

Voet et al., Biochemistry, Chapter 1: Life, pp. 3–4 & 7.

* cited by examiner

*Primary Examiner*—Kenneth R. Horlick
*Assistant Examiner*—Cynthia Wilder
(74) *Attorney, Agent, or Firm*—David G. Conlin; Kathryn A. Piffat; Edwards & Angell, LLP

(57) ABSTRACT

In accordance with the present invention, there is provided a device, method and kit for detecting any genetic material containing moieties. The present invention enables identification of known or unknown virions or bacteria contained in a fluid therein, such as virions in a blood sample. It also provides for an amenable and highly automatable device for massed screenings and the discovery of sequence variants of known virions, previously undetected virions, and other genetic material containing moieties. In one embodiment, the present invention utilizes at least one primer for analysis.

48 Claims, 2 Drawing Sheets

METHODS AND MATERIALS FOR DETECTING GENETIC MATERIAL

CROSS-REFERENCE TO RELATED APPLICATION

This application claims priority of U.S. Provisional Application Ser. No. 60/336,005, filed Nov. 15, 2001.

FIELD OF THE INVENTION

The present invention relates to the field of biological material detection and specifically to a device, method and kit for detecting a virus in biological fluids.

BACKGROUND OF THE INVENTION

Currently, screening of virions is accomplished through various methods and materials. One method is reverse transcription-polymerase chain reaction ("RT-PCR") based screening of virions wherein highly specific primers are utilized. Use of highly specific primers, though, has disadvantages. For example, only certain species of virions can be found, and failure to find extreme sequence variants of those species occasionally occurs.

The typical, conventional procedure for viral detection is to reverse transcribe the RNA with an RT primer close in proximity to the sequence to be amplified, followed by PCR amplification with a very specific set of primers and conditions, so that a highly specific amplification of a section of the chosen genome occurs. Alternatively, random primer sequences are used for RT-PCR, but these often have very low amplification efficiencies, and the unused primers can interfere with analysis via DNA array methods.

The first method described above for RT-PCR based screening of virions is predicated on the use of highly specific primers for purposes of amplification. Highly specific primers have the disadvantages of (a) only finding one species of virion and (b) occasionally failing to find extreme sequence variants of those species. The second method, using non-specific RT-PCR amplification with random primers, has neither of these problems, but is impractical for purposes of large and specific amplification.

Numerous materials are used in the screening of virions. FTA™ coated materials developed by Flinders University in Australia have been utilized for the preparation of genetic material. FTA™ materials and techniques yield highly purified genetic material bound to the cellulosic base filter for the duration of amplification reactions and other subsequent applications. FTA™ coated base filter materials include, but are not limited to filter paper, Whatman cellulosic BFC-180, 31-ET, glass microfiber, and any other similar filter materials known to those of skill in the art.

Genetic material can be purified from FTA™-coated material and then eluted from the material using a combination of water and elevated temperatures. The released genetic material is a soluble fragment of variable length that is suitable for any manner of amplification and detection methodologies. The elution of the genetic material is important in applications that would not be possible if the genetic material remained bound to the FTA™ coated material. As previously mentioned, FTA™ coating can be included on or within other filter membrane materials, additionally including, but not limited to, GF/F, GF/B, QMB, Anopore, alumina, GF/M, magnetic impregnated, meltblown polymerics, and surface modified polymerics. These filter membranes can yield superior binding capacity, ease of elution, and extended storage of genetic material.

Currently, there is a great need for the detection of traces of nucleic acids from pathogens, such as HIV or hepatitis, in the blood and other biological samples and for highly-sensitive, but broad-specificity, procedures. Essentially, general methods are required for detecting and typing almost any virion in body fluids, such as by the detection of DNA or RNA.

SUMMARY OF THE INVENTION

In accordance with the present invention, there is provided a device, method and kit for detecting any genetic material containing moieties. Specifically, the present invention focuses on identifying known or unknown virions contained in a fluid therein.

In one aspect, the present invention provides a method for analysis of a nucleic acid containing moiety in a biological sample, the method comprising:
 a. obtaining a biological sample;
 b. applying the biological sample to a dry solid medium, wherein the dry solid medium comprises a solid matrix having sorbed thereto a composition comprising a detergent;
 c. isolating nucleic acid components in the biological sample on the dry solid medium;
 d. providing at least one primer; and
 e. analyzing nucleic acid components from the biological sample using at least one primer.

In another aspect, the invention provides a device for storage and analysis of a nucleic acid containing moiety in a biological sample, the device comprising a plurality of layers comprising:
 a. a filter layer comprising a dry solid medium comprising a hydrophilic solid matrix; and
 b. an isolation layer comprising a dry solid medium comprising a neutral solid matrix having sorbed thereto a composition comprising a detergent.

In another aspect, the present invention provides a device for storage and analysis of a nucleic acid containing moiety in a biological sample, the device comprising a plurality of layers comprising:
 a. a collection layer comprising dry solid medium comprising a neutral porous matrix and a dry anticoagulant or liquefying agent;
 b. a filter layer comprising a dry solid medium comprising a solid matrix having a particle size limit that precludes eukaryotic cells, but not prokaryotic cells or virions;
 c. an isolation layer comprising a dry solid medium comprising a neutral solid matrix having sorbed thereto a composition comprising a detergent.

In another aspect, the present invention provides a method for storage and analysis of a nucleic acid containing moiety in a biological sample, the device comprising a plurality of layers comprising:
 a. applying a biological sample to a filter layer comprising a dry solid medium comprising a hydrophilic solid matrix;
 b. filtering the components of the biological sample through the filter layer to an isolation layer comprising a dry solid medium comprising a neutral solid matrix having sorbed thereto a composition comprising a detergent;
 c. retaining nucleic acid components in the isolation layer while removing the plurality of non-nucleic acid components;

d. drying the isolation layer;

e. providing a primer; and f. analyzing the nucleic acid components using at least one primer.

In another aspect, the invention provides a method for storage and analysis of a nucleic acid containing moiety in a biological sample, the device comprising a plurality of layers comprising:

a. applying a biological sample to a collection layer comprising a neutral porous matrix and a dry anticoagulant or liquefying agent;

b. filtering the remaining components of the biological sample through the collection layer to a filter layer comprising a dry solid medium comprising a solid matrix having a particle size limit that precludes eukaryotic cells, but not prokaryotic cells or virions;

c. filtering the remaining components of the biological sample through the filter layer to a separator layer;

d. filtering the remaining components of the biological sample through the an isolation layer comprising a dry solid medium comprising a neutral solid matrix having sorbed thereto a composition comprising a detergent;

e. retaining nucleic acid components in the isolation layer while removing the plurality of non-nucleic acid components;

f. drying the isolation layer;

g. providing at least one primer; and h. analyzing the nucleic acid components using PCR techniques, wherein two PCR primers are used.

In another aspect, the present invention provides a kit for storage and analysis of a nucleic acid containing moiety in a biological sample, wherein the kit comprises:

a. a device for storage and analysis of a nucleic acid containing moiety in a biological sample, the device comprising a plurality of layers comprising:
   i. a filter layer comprising a dry solid medium comprising a hydrophilic solid matrix; and
   ii. an isolation layer comprising a dry solid medium comprising a neutral solid matrix having sorbed thereto a composition comprising a detergent; and b. at least one primer for PCR.

In another aspect, the present invention provides a kit for storage and analysis of a nucleic acid containing moiety in a biological sample, wherein the kit comprises:

a. the device comprising a plurality of layers comprising:
   i. a collection layer comprising dry solid medium comprising a neutral porous matrix and a dry anticoagulant or liquefying agent;
   ii. a filter layer comprising a dry solid medium comprising a solid matrix having a particle size limit that precludes eukaryotic cells, but not prokaryotic cells or virions;
   iii. an isolation layer comprising a dry solid medium comprising a neutral solid matrix having sorbed thereto a composition comprising a detergent; and b. at least one primer for PCR.

DESCRIPTION OF THE INVENTION

Figure 1:
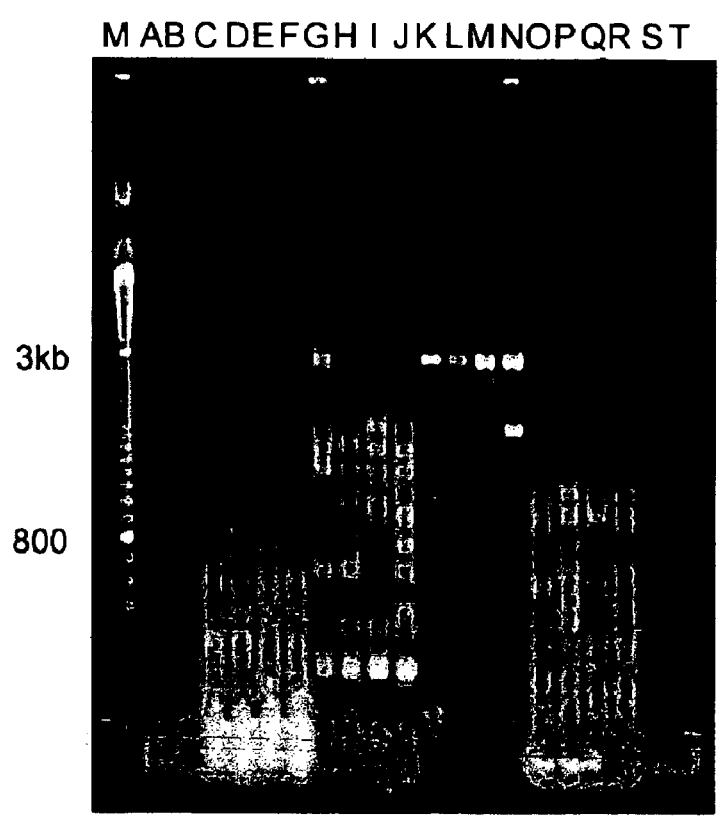
FIG. 1 Nucleic acid sequences in hepatitis C virus-contaminated human serum as amplification targets. This figure shows tracks of amplifications from an RT-PCR amplification of the type described in Example 1, using a long reverse-transcription and various low-specificity PCR conditions with a long-range PCR. In this example, all the primers are from the hepatitis C genome (an RNA virion), and the serum stored on an FTA™ paper is contaminated with hepatitis C.
Figure 2:
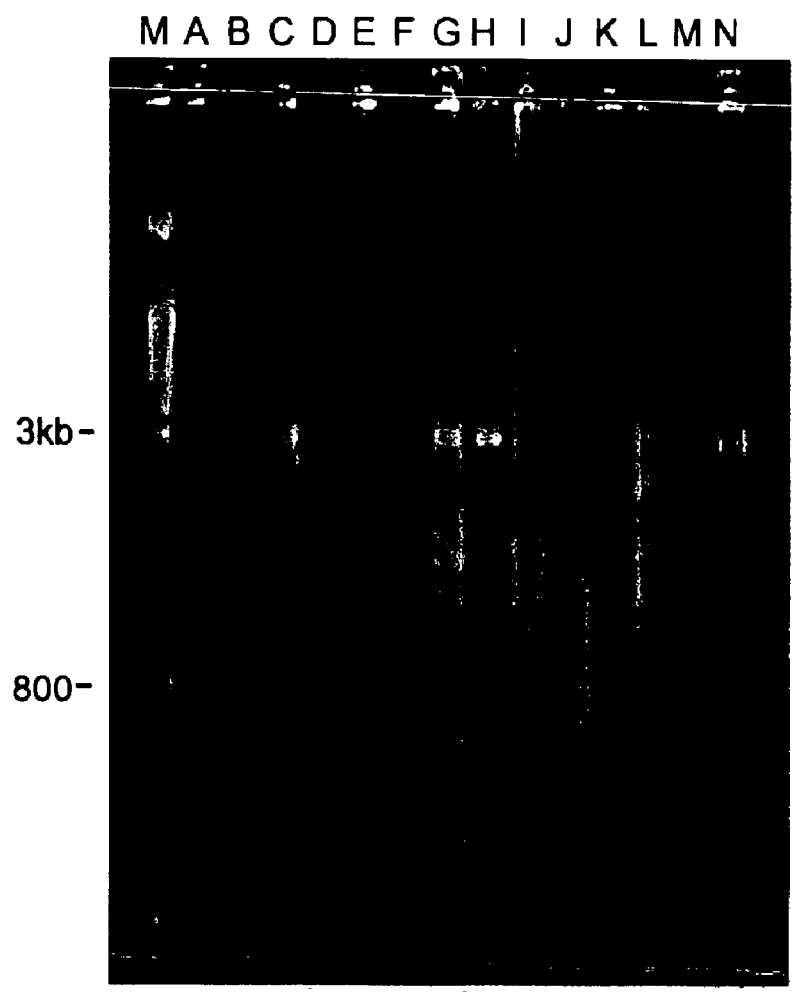
FIG. 2 Nucleic acid sequences in Coxsackie virus-contaminated human serum as amplification targets for unrelated primer sequences. This figure shows a wide range of molecular weight products formed in some tracks displayed as longitudinal smears or band patterns down the tracks. Some primer sets generated no bands, while others gave the desired banded smears, confirming that a very broad sample of the non-homologous virus genome has been amplified.

Generally, the present invention provides for an amenable and highly automatable device for massed screenings and discovery of sequence variants of known virions, previously undetected virions, and other genetic material containing moieties in fluids. The present invention further provides for a method and kit. While specific embodiments are disclosed herein, they are not exhaustive and can include other suitable designs that can be used on whole blood, serum, biological fluids, and any other similar fluids known to those of skill in the art. Additionally, other suitable designs include, but are not limited to, detecting virions, RNA, DNA, bacteria, and any other similar genetic material containing moieties known to those of skill in the art. Although some preferred embodiments utilize FTA™ coated material in a manner that is amenable to distance-collection and automatable with extremely broad and useful applications, the present invention can utilize any type of medium that binds or holds genetic material. Basically, any differing design, process, structure, and composite materials known to those of skill in the art can be utilized without departing from the spirit of the present invention.

In a preferred embodiment, a device is disclosed wherein a filter with genetic material binding qualities is used to collect blood, serum, saliva, biological fluids, and any other similar fluids. In a preferred embodiment, the filter used is a FTA™ coated filter. The device is designed to have the sample fluid placed on the filter for subsequent processing of virions, RNA, DNA, and other genetic material. In one embodiment, the present invention provides a disposable filter device and has a composite of layers to which the sample fluid is applied. The sample fluid is applied to a neutral layer, and the fluids are pulled through the neutral filter layer into another layer having capturing qualities.

In one aspect, the present invention provides a method for analysis of a nucleic acid containing moiety in a biological sample, the method comprising:

a. obtaining a biological sample;

b. applying the biological sample to a dry solid medium, wherein the dry solid medium comprises a solid matrix having sorbed thereto a composition comprising a detergent;

c. isolating nucleic acid components in the biological sample on the dry solid medium;

d. providing at least one primer; and e. analyzing nucleic acid components from the biological sample using at least one primer.

In one embodiment, the nucleic acid containing moiety is either a prokaryote or a virion.

In one embodiment, the nucleic acid components comprise DNA and are analyzed using PCR, more preferably wherein two PCR primers are used, at least one of which is non-specific.

In another embodiment, the nucleic acid components comprise RNA and are analyzed using RT-PCR, more preferably wherein no more than three RT-PCR primers are used, of which at least one primer is non-specific.

In another embodiment, the nucleic acid components are analyzed using DNA array techniques.

In another aspect, the present invention provides a device for storage and analysis of a nucleic acid containing moiety in a biological sample, the device comprising a plurality of layers comprising:
  a. a filter layer comprising a dry solid medium comprising a hydrophilic solid matrix; and
  b. an isolation layer comprising a dry solid medium comprising a neutral solid matrix having sorbed thereto a composition comprising a detergent.

In a preferred embodiment, the detergent is SDS.

In a preferred embodiment, the filter layer further comprises an anticoagulant, such as either EDTA or Tris-EDTA, or a liquefying agent, such as thiol.

In one embodiment, the composition of the isolation layer further comprises:
  a. a weak base (preferably Tris);
  b. a chelating agent (preferably EDTA); and
  c. optionally, uric acid or a urate salt.

In one embodiment, the isolation layer further comprises a primer.

In another preferred embodiment, the device further comprises a cap, wherein the cap comprises:
  i. a capping layer comprising a general denaturing agent (preferably SDS); and
  ii. an adhesive edge.

In yet another preferred embodiment, the general denaturing agent comprises:
  a. a weak base (preferably Tris);
  b. a chelating agent (preferably EDTA);
  c. an anionic surfactant or detergent (preferably SDS); and
  d. optionally, uric acid or a urate salt.

An example of such a preferred embodiment would be an FTA™ agent (Whatman, Inc.).

In another aspect, the present invention provides a device for storage and analysis of a nucleic acid containing moiety in a biological sample, the device comprising a plurality of layers comprising:
  a. a collection layer comprising dry solid medium comprising a neutral porous matrix and a dry anticoagulant or liquefying agent;
  b. a filter layer comprising a dry solid medium comprising a solid matrix having a particle size limit that precludes eukaryotic cells, but not prokaryotic cells or virions;
  c. an isolation layer comprising a dry solid medium comprising a neutral solid matrix having sorbed thereto a composition comprising a detergent.

In a preferred embodiment, the device further comprises a cap, wherein the cap comprises:
  i. a capping layer comprising a general denaturing agent; and
  ii. an adhesive edge.

In another preferred embodiment, the device further comprises a separator layer between the filter layer and the isolation layer.

In another preferred embodiment, the filter layer further comprises an anticoagulant or a liquefying agent.

In various preferred embodiments of the device, the detergent is SDS, the anticoagulant is either EDTA or Tris-EDTA, the liquefying agent is thiol, and/or the general denaturing agent is SDS. Additional preferred embodiments of the device are outlined above.

In another aspect, the present invention provides a method for storage and analysis of a nucleic acid containing moiety in a biological sample, the device comprising a plurality of layers comprising:
  a. applying a biological sample to a filter layer comprising a dry solid medium comprising a hydrophilic solid matrix;
  b. filtering the components of the biological sample through the filter layer to an isolation layer comprising a dry solid medium comprising a neutral solid matrix having sorbed thereto a composition comprising a detergent;
  c. retaining nucleic acid components in the isolation layer while removing the plurality of non-nucleic acid components;
  d. drying the isolation layer;
  e. providing a primer; and
  f. analyzing the nucleic acid components using at least one primer.

In another aspect, the present invention provides a method for storage and analysis of a nucleic acid containing moiety in a biological sample, the device comprising a plurality of layers comprising:
  a. applying a biological sample to a collection layer comprising a neutral porous matrix and a dry anticoagulant or liquefying agent;
  b. filtering the remaining components of the biological sample through the collection layer to a filter layer comprising a dry solid medium comprising a solid matrix having a particle size limit that precludes eukaryotic cells, but not prokaryotic cells or virions;
  c. filtering the remaining components of the biological sample through the filter layer to a separator layer;
  d. filtering the remaining components of the biological sample through the separator layer to an isolation layer comprising a dry solid medium comprising a neutral solid matrix having sorbed thereto a composition comprising a detergent;
  e. retaining nucleic acid components in the isolation layer while removing the plurality of non-nucleic acid components;
  f. drying the isolation layer;
  g. providing at least one primer; and
  h. analyzing the nucleic acid components using PCR techniques, wherein two PCR primers are used.

Preferably, at least one of the primers is non-specific. Additional preferred embodiments are described above with respect to the devices provided by the present invention.

In a preferred embodiment, the detergent is SDS.

In a preferred embodiment, the filter layer further comprises an anticoagulant, such as either EDTA or Tris-EDTA, or a liquefying agent, such as thiol.

In one embodiment, the composition of the isolation layer further comprises:
  a. a weak base (preferably Tris);
  b. a chelating agent (preferably EDTA); and
  c. optionally, uric acid or a urate salt.

In one embodiment, the isolation layer further comprises a primer.

In another preferred embodiment, the device further comprises a cap, wherein the cap comprises:

i. a capping layer comprising a general denaturing agent (preferably SDS); and
ii. an adhesive edge.

In yet another preferred embodiment, the general denaturing agent comprises:
a. a weak base (preferably Tris);
b. a chelating agent (preferably EDTA);
c. an anionic surfactant or detergent (preferably SDS); and
d. optionally, uric acid or a urate salt.

An example of such a preferred embodiment would be an FTA™ agent (Whatman, Inc.).

In another aspect, the present invention provides a kit for storage and analysis of a nucleic acid containing moiety in a biological sample, wherein the kit comprises:
a. a device for storage and analysis of a nucleic acid containing moiety in a biological sample, the device comprising a plurality of layers comprising:
   i. a filter layer comprising a dry solid medium comprising a hydrophilic solid matrix; and
   ii. an isolation layer comprising a dry solid medium comprising a neutral solid matrix having sorbed thereto a composition comprising a detergent; and
b. at least one primer for PCR.

In another aspect, the present invention provides a kit for storage and analysis of a nucleic acid containing moiety in a biological sample, wherein the kit comprises:
a. the device comprising a plurality of layers comprising:
   i. a collection layer comprising dry solid medium comprising a neutral porous matrix and a dry anticoagulant or liquefying agent;
   ii. a filter layer comprising a dry solid medium comprising a solid matrix having a particle size limit that precludes eukaryotic cells, but not prokaryotic cells or virions;
   iii. an isolation layer comprising a dry solid medium comprising a neutral solid matrix having sorbed thereto a composition comprising a detergent; and
b. at least one primer for PCR.

The present invention further includes a method detecting genetic material containing moieties. The method involves using the device disclosed herein and has several steps. The initial step includes placing a fluid sample of blood, saliva, or other biological fluid on the hydrophilic membrane. By capillary action, centrifugal assistance, and any other similar technique known to those of skill in the art, the fluid sample is then drawn into the FTA™ layer through the hydrophilic membrane. Any cells left on the hydrophilic membrane die thereafter. The fluid loaded device is then stored desiccated until processing occurs. The drying process includes, but is not limited to exposure to a dry atmosphere or with the aid of a desiccant such as silica gel or other similar drying agent.

A detection process can occur through any number of methods and processes that include, but are not limited to reverse transcription followed by subsequent PCR procedures. The procedures can occur in a single tube through the use of SDS papers such as FTA™-coated materials or papers simply comprising a detergent, such as SDS. Additionally, the procedures can be carried out on multi-well plate devices or any other similar devices known to those of skill in the art.

The detection process further includes the use of various primer sequences that are either labeled or unlabeled according to the mode of operation of the DNA array. As previously stated, the preferred embodiment uses a reverse transcriptase primer and reverse transcription conditions are primarily used. Furthermore, a pair of selected sequences from known virions is optimally used, but under conditions of slightly lower stringency such that many unrelated sequences are also amplified.

The next step, after obtaining amplified sequence products of the PCR process, the sequences are ethidium-stained on a standard, low-resolution gel to prove the existence of the various sequences. Of course, capillary electrophoresis, high-resolution acrylamide gel systems, or any other method known to those of skill in the art can be used. As a result of the gel electrophoresis, the various sequences of virions having either DNA or RNA can be identified through an analysis of the pattern of bands existing on the gel. Many array elements can be included for each of the common virions. The reactive array elements can show novel patterns and stimulate more detailed study of the dried serum sample. Furthermore, amplification of totally novel virions can be detected by cross-reaction with sequences from known virions.

The invention has been described in an illustrative manner, and it is to be understood that the terminology, which has been used, is intended to be in the nature of words of description rather than of limitation.

Obviously, many modifications and variations of the present invention are possible in light of the above teachings. It is, therefore, to be understood that within the scope of the desired invention, the invention may be practiced otherwise than as specifically described.

EXAMPLE 1

Methods

An automatable protocol for detecting almost any virus, particularly sequence variants of known virions or previously undescribed virions or similar moieties in human serum or other biological fluid.

Applications: Applications include, but are not limited to, field studies of virions or routine diagnostics. In mass surveys, the detection of sequence variants of known virions or previously undetected virions or other nucleic acid containing moieties in biological fluids by a protocol that is highly automatable and thus amenable to massed screenings and discovery.

In one embodiment, this protocol is particularly useful for surveying serum produced by centrifugation or by the filtering device proposed by the present invention, but is not limited to the use of serum or to the device of the present invention.

This embodiment of the present invention is amenable to distance-collection and is highly automatable with an extremely useful and very broad application. This particular example has several features:

Processing for RNA.

Low specificity, high-gain amplification using a very few primers (but not random primers) and, in the embodiment described in this example, long-range PCR.

The degree of specificity can be optimized for general use from the choice of amplification conditions, generalized to the choice of the contours of an amplification-conditions ramp.

Final data-analysis by DNA-arrays.

It can detect known or unknown virions, either RNA or DNA with equal speed and ease. It can also be used to detect bacteria.

Collection of samples: It is preferable that gross nuclear DNA and mitochondrial DNA are absent as far as practical from the starting material. Thus, a sample of human serum is obtained at some site remote from the processing laboratory by the use of a small transportable centrifuge or by disposable filters. "Filterable" virions are often the only nucleic acid in centrifuged or filtered biological fluids.

Preservation and transport: The gross-DNA-free sample, e.g., serum sample is placed on a transport paper, such as FTA™ paper, and dried by a dry atmosphere or if humidity is high, with the aid of a desiccant such as silica gel. Optionally, it may then be mailed with its desiccant to a processing laboratory. Examples of suitable dry solid media are found in U.S. Pat. No. 5,756,126 (May 26, 1998) (Burgoyne); U.S. Pat. No. 5,807,527 (Sep. 15, 1998) (Burgoyne); and U.S. Pat. No. 5,972,386 (Oct. 26, 1999) (Burgoyne). The disclosures of the patents are incorporated by reference herein.

Fluids containing virions may be transported dry on protein-denaturing papers with preservation of the RNA or DNA on them, as described in Rogers and Burgoyne (Roger, C. D. & L. A. Burgoyne (2000), "Reverse transcription of an RNA genome from databasing paper (FTA®)," Biotechnol. Appl. Biochem. 31 (Pt.3): 219–224), the disclosure of which is incorporated by reference herein. Examples of work with bacteria are described in Rogers and Burgoyne (Rogers, C. & L. Burgoyne (1997), "Bacterial typing: storing and processing of stabilized reference bacteria for polymerase chain reaction without preparing DNA—an example of an automatable procedure," Anal. Biochem. 247 (2): 223–227), the disclosure of which is incorporated likewise by reference herein.

Processing for RT-PCR: A disc of denaturing, nucleic acid preserving paper may be used. Nucleic acid-containing fluids, such as those that have traces of RNA virions, may be processed for reverse transcription and subsequent PCR in a single tube, without removing the disc of paper, by the use of SDS-containing papers, such as FTA™ papers, as described in Rogers and Burgoyne (2000) (cited above). Agitation of the tubes during washings is also described in Rogers and Burgoyne. Alternatively, a protocol of heating and cooling may be performed so that convective washing takes place. It is envisioned that this procedure can also be performed using a multi-well plate device with each disc held in one place of the device and washing by slow filtration.

Primers: Primers may be labeled or unlabeled according to the mode of operation of the DNA array and many sequences will be suitable as primers. Examples are provided here, but alternatives within the scope of the present invention are readily understood by those of ordinary skill in the art.

In this example, a reverse transcription primer is used to perform reverse transcription, such that the whole genome or a major sample of it is transcribed into DNA. Then, a pair of selected sequences is used for PCR amplification.

Primers used in Examples 1A and 1B are shown in Table 1.

TABLE 1

Primers used in Examples 1A and 1B.

| Name | Sequence | (SEQ ID NO:_) |
|---|---|---|
| HepCP2 | 5'-GTTTATCCAAGAAAGGACCCG-3' | (SEQ ID NO:1) |
| HCP1 | 5'-GTAGACCGTGCA(A/T/C)CATGA-3' | (SEQ ID NO:2) |
| HCP2 | 5'-TGACTAGGGCTAAGATGGAG-3' | (SEQ ID NO:3) |
| HP6 | 5'-CAGCCTCCAGGACCCCC-3' | (SEQ ID NO:4) |
| HP7 | 5'-GTCTAGCCATGGCGTTA-3' | (SEQ ID NO:5) |
| Hep-CFSP | 5'-GCACTCTCTGCAGTCATG-3' | (SEQ ID NO:6) |
| EP1 | 5'-ATTGTCACCATAAGCAGCCA-3' | (SEQ ID NO:7) |

EXAMPLE 1A

In this example, the primer sequences were from known virions (Table 2), but conditions of slightly lower stringency were used, such that many unrelated sequences were also amplified (FIG. 1). The sequences of the primers are derived from sequences from the published hepatitis C genome and were used to amplify nucleic acids in human serum. One of ordinary skill in the art can obtain additional hepatitis C sequences, or sequences from a wide range of nucleotide sequences of interest from various species, which have been deposited in BLAST or a similar nucleotide database.

TABLE 2

Primer sequences used for amplifications in FIG. 1.

| Sample | Primer Combinations | DMSO (%) |
|---|---|---|
| A | HepCP2 & HP6 | 0 |
| B | HepCP2 & HP6 | 0 |
| C | HepCP2 & HP6 | 0 |
| D | HCP2 & HCP1 | 0 |
| E | HCP2 & HP6 | 0 |
| F | HCP2 & HP7 | 0 |
| G | HepCP2 & HP6 | 1 |
| H | HCP2 & HCP1 | 1 |
| I | HCP2 & HP6 | 1 |
| J | HCP2 & HP7 | 1 |
| K | HepCP2 & HP6 | 2 |
| L | HCP2 & HCP1 | 2 |
| M | HCP2 & HP6 | 2 |
| N | HCP2 & HP7 | 2 |
| O | HepCP2 & HP6 | 3 |
| P | HCP2 & HCP1 | 3 |
| Q | HCP2 & HP6 | 3 |
| R | HCP2 & HP7 | 3 |
| S | HepCP2 & HP6 | 0 |
| T | HepCP2 & HP6 | 0 |

In this Example, serum from a human containing the hepatitis C virus served as the source of amplification target. FIG. 1 shows tracks of amplifications from an RT-PCR amplification of the type described herein, using a long reverse transcription and various low-specificity PCR conditions with a long-range PCR. In this example, all the primers are from the hepatitis C genome (an RNA virion), and the serum stored on an FTA™ paper is contaminated with hepatitis C.

Processing of the Amplified Sequences: FIG. 1 shows the PCR products on a standard, ethidium-stained, low-resolution gel. Alternatively, in automated, high-throughput laboratories, the analysis preferably would be performed on a DNA array with bands being produced using, for example, fluorescent primers so that the DNA-array elements would become labeled with a unique pattern for each virus, known or unknown. In fact, the diversity of high molecular weight species in FIG. 1 likewise indicates an application for DNA arrays. As only three primers are used, the binding of free primer and primer dimer can be taken into account during analysis. Alternatively, the binding of free primer and primer dimer formation are simply blocked with, for example, addition of unlabeled, identical primer sequences to the mixture exposed to the DNA array.

Analysis of Data: The pattern of labeling of the array elements is diagnostic of the sequences amplified, and these are a sample of the virions sequences. Many array elements could be included for each of the common virions both DNA and RNA. This method would enable identification both of the virions and of sequences from contaminating small genomes, such as the mitochondrial genome released from broken blood platelets. The reactive array elements would also show novel patterns, which would permit a more detailed study of the dried serum sample, such as by cloning and/or sequencing bands from the amplification described above.

The amplification of totally novel virions would be detected by cross-reaction with sequences from known virions without a pattern match. If totally novel moieties were being sought, then such a cross-reaction should have many possibilities and/or a high resolution gel may be run on the same sample. It is not necessary to amplify all of the virion sequences equally well. Non-random amplification of, for example, only 20% to 70% of the virion's genome could be quite suitable for characterization of the virus as long as the amplification conditions are well standardized.

Although reverse transcription is used in this example, the present invention also provides a method that will detect known or novel DNA virions.

EXAMPLE 1B

Although similar bands might possibly be obtained from random primers, random primers would be expected to block the DNA array badly or with insufficient discrimination. Therefore, non-random primers are preferred, even non-random, unrelated primers, such as those listed in Table 3, which were used to obtain the results shown in FIG. 2. The sequences of the primers used as "non-specific" primers for purposes of this set of amplifications are derived from sequences from the published hepatitis C genome and the CVB genome and were used to amplify nucleic acids in human serum. One of ordinary skill in the art can obtain additional hepatitis C and CVB sequences deposited in a nucleotide database, such as BLAST, as can other types of specific or non-specific sequences according to the needs of the researcher.

TABLE 3

Primer sequences used for amplifications in FIG. 2.

| | Sample | 1st Strand Primer | Primer Combination | Annealing Temp. (° C.) |
|---|---|---|---|---|
| A | HepC | HepCFSP | HCP2 & HCP1 | 48 |
| B | HepC | HepCFSP | HCP2 & HP7 | 48 |
| C | HepC | HepCFSP | HCP2 & HCP1 | 45 |
| D | HepC | HepCFSP | HCP2 & HP7 | 45 |
| E | HepC | HepCFSP | HCP2 & HCP1 | 42 |
| F | HepC | HepCFSP | HCP2 & HP7 | 42 |
| G | HepC | HepCFSP | HCP2 & HCP1 | 40 |
| H | HepC | HepCFSP | HCP2 & HP7 | 40 |
| I | CVB-4 | EP1 | HCP2 & HCP1 | 40 |
| J | CVB-4 | EP1 | HCP2 & HP6 | 40 |
| K | CVB-4 | EP1 | HCP2 & HP7 | 40 |
| L | CVB-4 | HepCFSP | HCP2 & HCP1 | 40 |
| M | CVB-4 | HepCFSP | HCP2 & HP6 | 40 |
| N | CVB-4 | HepCFSP | HCP2 & HP7 | 40 |

In this Example, serum from a human containing the Coxsackie virus served as the source of amplification target for unrelated primer sequence (e.g., primer sequences used as the "non-specific" primer sequences). FIG. 2 shows a wide range of molecular weight products formed in some tracks displayed as longitudinal smears or band patterns down the tracks. Some primer sets generated no bands, while others gave the desired banded smears, confirming that a very broad sample of the on-homologous virus genome has been amplified. In this example, the serum was stored on FTA™ paper. Primer EP1 was selected for specificity to a highly conserved region of the 5'-non-coding region (5'-NCR) of Coxsackie virus B4 (CVB-4) for first strand synthesis of samples I–K. The remaining primers used in this example were designed from the published Hepatitis C genome.

Patterns of bands can also be detected by capillary electrophoresis or high resolution arcylamide gel systems.

EXAMPLE 2

Devices

A combined serum and/or saliva collecting filter with isolation, storage, and transport properties.

The device described in this example is one embodiment of the present invention. It can be viewed as essentially, a disposable or "field" substitute for a microcentrifuge. For example, it can be used to isolate serum on a storage/transport paper, such as an FTA™ paper, for 1 mm punch processing of RNA or DNA from virions.

In one preferred embodiment, the present invention provides a disposable filter device comprising a composite of layers that has whole blood applied to its top layer such that the blood fluids are pulled through the top filter layer into an isolation/storage/transport layer, such as an FTA™ layer.

EXAMPLE 3

An Example of a Two-layer Embodiment

Basically a piece of paper capable of disrupting proteins and/or membranes, such as a storage or transport paper comprising a detergent (e.g., FTA™ paper comprising sodium dodecyl sulfate (SDS) ($C_{12}$)), is paired with a hydrophilic membrane or pad having pores slightly smaller than blood platelets. The membrane comprises an anticoagulant, such as ethylenediaminetetra-acetic acid (EDTA). Blood is placed on the membrane side, and serum is drawn by capillary action into the paper layer. Other detergents and agents include, but are not limited to, SDS (lauryl), alkyl aryl sulfonates, long chain (Fatty) alcohol sulfates, olefine sulfates, sulfosuccinates, phosphate esters, sodium 2-ethylhexysulfate, polyvinyl sulfate, polyacrylate, polyphosphate, sodium polyacrylate, sodium polyvinyl sulfate, and any other similar detergents and polyanions known to those of skill in the art.

If, for example, the device utilizes FTA™ paper or a similar type of storage or transport paper comprising SDS, the device is sterilized by the back-diffusion of SDS from the FTA™ or other paper, through the membrane after the filtering process is over.

Mode of Operation: Blood or saliva placed on the filter layer would have its serum drawn into the storage or transport paper layer, leaving the cells on the filter. If, for example, the device utilizes FTA™ paper or a similar type of storage or transport paper comprising SDS, then once filtration has stopped, SDS would diffuse from the paper layer back through the filter and also kill the cells left on the filter.

Preferably, the blood-loaded device is stored desiccated until processing.

EXAMPLE 4

An Example of a Four-layer Embodiment

The present invention can also be practiced using more complex arrangements of layers. One example of a four-layer embodiment comprises the following layers:

a. Layer #1—The collection layer (to which blood or saliva will be applied) that is a neutral porous material, such as blotting paper or filter paper comprising a dry anticoagulant, such as Tris-EDTA, preferably in a low concentration (such as approximately 0.05–0.5 mM, more preferably approximately 0.1 mM), and if saliva is to be used, optionally also comprising a liquefying agent, such as thiol.

b. Layer #2—The filter layer having a particle size limit that precludes blood platelets but not virions. This layer serves primarily for purposes of separation.

c. Layer #3 (optional)—A thin reagent-free layer acting as a separator and break-point between Layer #2 and Layer #4.

d. Layer #4—An collection, storage or isolation layer comprising a detergent, such as SDS, preferably at a high concentration (such as approximately 0.5–2% v/v). This layer also serves as a destination layer or repository layer that actually stores and protects the virion RNA or DNA or other types of RNA or DNA, such as those of bacterial origin.

Optionally a cap may also be provided. The cap sits on one side of the device so it can be folded over on top of the device and act as a stopper or barrier after use, and having a capping layer or sachet that contains a general denaturant (preferably SDS in a high concentration, as described above) and an adhesive edge for sealing the top of the apparatus after it has operated so that the upper side of the device is sterilized after the device has finished operating. Preferably, this cap should not be closed until the device has had a few seconds to operate, and the cap should have an extremely strong capillary effect such that it causes capillary flow to reverse towards it.

In general, therefore, this embodiment of the device includes multiple layers of material. An initial layer would be a collection layer to which the fluid sample would be applied. This layer can be a bland, neutral, porous material such as blotting paper or filter paper with only a low amount of dry anticoagulant. The anticoagulant includes, but is not limited to EDTA, Tris-EDTA, or any other similar chemical composition with anticoagulant properties known to those of skill in the art. The initial layer can additionally have a liquefying agent including, but not limited to thiol and any other similar liquefying agent known to those of skill in the art.

The second layer precludes cells such as blood platelets, but not virions or other similarly sized particles, from passing through to the next layer. The second layer is critical for proper separation of desired virions or other genetic material containing moieties. A third, optional layer can be a thin reagent-free layer acting as a separator and break point between the second and final, fourth layer. The third layer is made of any material that includes paper, filter, or any other similar porous material known to those of skill in the art. The final, fourth layer is a FTA™ coated material. The FTA™ coated material can have a very high amount and concentration of dodecyl sulfate or other similar material known to those of skill in the art. This final layer is the final destination and repository of the virions or other genetic material containing moieties. The final layer stores the virion RNA or DNA.

Additionally, the filter layer combination may be contained within a sachet, pouch, bag, vial, tube, or other similar containing device known to those of skill in the art. The sachet has a cap or cover held by a tag to the main device, but away from the device. The device is removed and the drop of blood from a finger-stick is placed on the first layer, the neutral layer. The blood wets the layer and then is drawn through the membrane where the platelets and cells are removed and the serum moves into the FTA™ layer beneath where the virus dries and is preserved. Afterwards, the porous stopper layer impregnated with SDS, other similar chemical composition or the full FTA™ mix is then used to block the top. This sterilizes the recipient layer and makes it suitable for storage of the genetic material. The device is stored desiccated until subsequent processing or applications occur.

EXAMPLE 5

Description of Device's Operation in One Preferred Two-layer Embodiment with Additional Stopper In one preferred embodiment, the whole device comes in sealed sachet with the cap held by a tag to the main device but away from the device.

The device is removed and the drop of blood, such as from a finger-stick, is placed on the first layer, which is the neutral layer. The blood wets this layer and then is drawn through the neutral layer whereby the platelets and cells are removed, and the serum moves into the storage layer beneath it, where the viral particle (or alternatively, bacterium or mitochondrion) dries and is preserved.

After use, the porous stopper layer impregnated with SDS or with the full FTA™ mix is used to block the top. This sterilizes the recipient storage layer and makes it suitable for storage of the viral (or alternatively, bacterial or mitochondrial) DNA or RNA.

The device is stored desiccated until processing.

Variations, modifications, and other implementations of what is described herein will occur to those of ordinary skill in the art without departing from the spirit and scope of the invention.

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

What is claimed is:

1. A device for storage and analysis of a nucleic acid containing moiety in a biological sample, the device comprising a plurality of layers comprising:
   a. a filter layer comprising a dry solid medium comprising a hydrophilic solid matrix; and
   b. an isolation layer comprising a dry solid medium comprising a neutral solid matrix having sorbed thereto a composition comprising a detergent.

2. The device of claim 1, wherein the detergent comprises SDS.

3. The device of claim 1, wherein the filter layer further comprises an anticoagulant or a liquefying agent.

4. The device of claim 3, wherein the anticoagulant comprises EDTA or Tris-EDTA.

5. A device for storage and analysis of a nucleic acid containing moiety in a biological sample, the device comprising a plurality of layers comprising:
   a. a filter layer comprising a dry solid medium comprising a hydrophilic solid matrix; and
      ii. an anticoagulant or liquefying agent comprising thiol; and
   b. an isolation layer comprising a dry solid medium comprising a neutral solid matrix having sorbed thereto a composition comprising a detergent.

6. The device of claim 1, wherein the composition of the isolation layer further comprises:
   a. a weak base;
   b. a chelating agent; and
   c. optionally, uric acid or a urate salt.

7. The device of claim 6, wherein the weak base comprises Tris.

8. The device of claim 6, wherein the chelating agent comprises EDTA.

9. The device of claim 1, wherein the isolation layer further comprises a primer.

10. A device for storage and analysis of a nucleic acid containing moiety in a biological sample, the device comprising a plurality of layers comprising:
    a. a filter layer comprising a dry solid medium comprising a hydrophilic solid matrix;
    b. an isolation layer comprising a dry solid medium comprising a neutral solid matrix having sorbed thereto a composition comprising a detergent; and
    c. a cap, wherein the cap comprises:
       i. a capping layer comprising a general denaturing agent; and
       ii an adhesive edge.

11. The device of claim 10, wherein the general denaturing agent comprises SDS.

12. The device of claim 10, wherein the general denaturing agent comprises:
    a. a weak base;
    b. a chelating agent;
    c. an anionic surfactant or detergent; and
    d. optionally, uric acid or a urate salt.

13. The device of claim 12, wherein the weak base comprises Tris.

14. The device of claim 12, wherein the chelating agent comprises EDTA.

15. The device of claim 12, wherein the detergent comprises SDS.

16. A device for storage and analysis of a nucleic acid containing moiety in a biological sample, the device comprising a plurality of layers comprising:
    a. a collection layer comprising dry solid medium comprising a neutral porous matrix and a dry anticoagulant or liquefying agent;
    b. a filter layer comprising a dry solid medium comprising a solid matrix having a particle size limit that precludes eukaryotic cells, but not prokaryotic cells or virions; and
    c. an isolation layer comprising a dry solid medium comprising a neutral solid matrix having sorbed thereto a composition comprising a detergent.

17. The device of claim 16, further comprising:
    d. a separator layer between the filter layer and the isolation layer.

18. The device of claim 16, wherein the detergent comprises SDS.

19. The device of claim 16, wherein the composition of the isolation layer of part b further comprises:
    a. a weak base;
    b. a chelating agent; and
    c. optionally, uric acid or a urate salt.

20. The device of claim 19, wherein the weak base comprises Tris.

21. The device of claim 19, wherein the chelating agent comprises EDTA.

22. The device of claim 16, wherein the isolation layer further comprises a primer.

23. The device of claim 16, wherein the filter layer further comprises an anticoagulant or a liquefying agent.

24. The device of claim 23, wherein the anticoagulant comprises EDTA or Tris-EDTA.

25. A device for storage and analysis of a nucleic acid containing moiety in a biological sample, the device comprising a plurality of layers comprising:
    a. a collection layer comprising dry solid medium comprising a neutral porous matrix and a dry anticoagulant or liquefying agent comprising thiol;
    b. a filter layer comprising a dry solid medium comprising a solid matrix having a particle size limit that precludes eukaryotic cells, but not prokaryotic cells or virions; and
    c. an isolation layer comprising a dry solid medium comprising a neutral solid matrix having sorbed thereto a composition comprising a detergent.

26. A device for storage and analysis of a nucleic acid containing moiety in a biological sample, the device comprising a plurality of layers comprising:
    a. a collection layer comprising dry solid medium comprising a neutral porous matrix and a dry anticoagulant or liquefying agent;
    b. a filter layer comprising a dry solid medium comprising a solid matrix having a particle size limit that precludes eukaryotic cells, but not prokaryotic cells or virions;
    c. an isolation layer comprising a dry solid median comprising a neutral solid matrix having sorbed thereto a composition comprising a detergent; and
    d. a cap, wherein the cap comprises:
       i. a capping layer comprising a general denaturing agent; and
       ii. an adhesive edge.

27. The device of claim 26, wherein the general denaturing agent comprises SDS.

28. The device of claim 26, wherein the general denaturing agent comprises:
    a. a weak base;
    b. a chelating agent;

c. an anionic surfactant or detergent; and d. optionally, uric acid or a urate salt.

29. The device of claim 28, wherein the weak base comprises Tris.

30. The device of claim 28, wherein the chelating agent comprises EDTA.

31. The device of claim 28, wherein the detergent comprises SDS.

32. A kit for storage and analysis of a nucleic acid containing moiety in a biological sample, wherein the kit comprises:

a. a device for storage and analysis of a nucleic acid containing moiety in a biological sample, the device comprising a plurality of layers comprising:

i. a filter layer comprising a dry solid medium comprising a hydrophilic solid matrix; and ii. an isolation layer comprising a dry solid medium comprising a neutral solid matrix having sorbed thereto a composition comprising a detergent; and b. at least one primer for PCR.

33. A kit for storage and analysis of a nucleic acid containing moiety in a biological sample, wherein the kit comprises:

a. the device comprising a plurality of layers comprising:

i. a collection layer comprising dry solid medium comprising a neutral porous matrix and a dry anticoagulant or liquefying agent;

ii. a filter layer comprising a dry solid medium comprising a solid matrix having a particle size limit that precludes eukaryotic cells, but not prokaryotic cells or virions; and iii. an isolation layer comprising a dry solid medium comprising a neutral solid matrix having sorbed thereto a composition comprising a detergent; and b. at least one primer for PCR.

34. A device for storage and analysis of a nucleic acid containing moiety in a biological sample, the device comprising a plurality of layers comprising:

a. a filter layer comprising a dry solid medium comprising a hydrophilic solid matrix having a particle size limit that precludes eukaryotic cells, but not prokaryotic cells or virions; and b. an isolation layer comprising a dry solid medium comprising a neutral solid matrix having sorbed thereto a composition comprising a detergent.

35. The device of claim 34, wherein the detergent comprises SDS.

36. The device of claim 34, wherein the filter layer further comprises an anticoagulant or a liquefying agent.

37. The device of claim 34, wherein the anticoagulant comprises EDTA or Tris-EDTA.

38. A device for storage and analysis of a nucleic acid containing moiety in a biological sample, the device comprising a plurality of layers comprising:

a. a filter layer comprising a dry solid medium comprising a hydrophilic solid matrix having a particle size limit that precludes eukaryotic cells, but not prokaryotic cells or virions; and b. an isolation layer comprising a dry solid medium comprising a neutral solid matrix having sorbed thereto a composition comprising a detergent;

wherein the filter layer further comprises an anticoagulant or a liquefying agent comprising thiol.

39. The device of claim 34, wherein the composition of the isolation layer further comprises:

a. a weak base;

b. a chelating agent; and c. optionally, uric acid or a urate salt.

40. The device of claim 39, wherein the weak base comprises Tris.

41. The device of claim 39, wherein the chelating agent comprises EDTA.

42. The device of claim 34, wherein the isolation layer further comprises a primer.

43. A device for storage and analysis of a nucleic acid containing moiety in a biological sample, the device comprising a plurality of layers comprising:

a. a filter layer comprising a dry solid medium comprising a hydrophilic solid matrix having a particle size limit that precludes eukaryotic cells, but not prokaryotic cells or virions;

b. an isolation layer comprising a dry solid medium comprising a neutral solid matrix having sorbed thereto a composition comprising a detergent; and c. a cap, wherein the cap comprises:

i. a capping layer comprising a general denaturing agent; and ii. an adhesive edge.

44. The device of claim 43, wherein the general denaturing agent of the capping layer comprises SDS.

45. The device of claim 43, wherein the general denaturing agent of the capping layer comprises:

a. a weak base;

b. a chelating agent;

c. an anionic surfactant or detergent; and d. optionally, uric acid or a urate salt.

46. The device of claim 45, wherein the weak base comprises Tris.

47. The device of claim 45, wherein the chelating agent comprises EDTA.

48. The device of claim 45, wherein the detergent comprises SDS.

* * * * *

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
```

<223> OTHER INFORMATION: Description of Artificial Sequence: Primer

<400> SEQUENCE: 1
gtttatccaa gaaaggaccc g                                              21

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 2
gtagaccgtg cahcatga                                                  18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
tgactagggc taagatggag                                                20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 4
cagcctccag gacccccc                                                  17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 5
gtctagccat ggcgtta                                                   17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
gcactctctg cagtcatg                                                  18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
attgtcacca taagcagcca                                                20